United States Patent von Deyn et al.

Patent Number: 5,972,841
Date of Patent: Oct. 26, 1999

[54] QUINOLINE-3-CARBOXAMIDES, THEIR MANUFACTURE AND USE

[75] Inventors: Wolfgang von Deyn, Neustadt; Hans Theobald, Limburgerhof; Christoph Nuebling, Hassloch; Uwe Kardorff, Mannheim; Helmut Walter, Obrigheim; Karl-Otto Westphalen, Speyer; Thomas Kappe, Graz; Matthias Gerber, Mutterstadt, all of Germany

[73] Assignee: BASF Aktiengesellschaft, Ludwigshafen, Germany

[21] Appl. No.: 08/988,765

[22] Filed: Dec. 11, 1997

Related U.S. Application Data

[62] Division of application No. 08/794,572, Feb. 3, 1997, Pat. No. 5,798,451, which is a continuation of application No. 08/542,136, Oct. 12, 1995, abandoned, which is a continuation of application No. 08/241,390, May 11, 1994, abandoned, which is a continuation of application No. 07/981,356, Nov. 25, 1992, abandoned.

Foreign Application Priority Data

Nov. 26, 1991 [DE] Germany .............................. 41 38 820

[51] Int. Cl.$^6$ .................................................. A01N 43/42
[52] U.S. Cl. .......................................................... 504/247
[58] Field of Search .................... 504/147, 149, 504/247; 546/155

[56] References Cited

U.S. PATENT DOCUMENTS

| | | | |
|---|---|---|---|
| 3,960,868 | 6/1976 | Ferrini et al. ............................. | 546/155 |
| 4,107,310 | 8/1978 | Allais et al. .............................. | 546/155 |
| 4,959,363 | 9/1990 | Wentland ................................. | 546/155 |

FOREIGN PATENT DOCUMENTS 152966  6/1990  Japan ..................... 546/155

OTHER PUBLICATIONS

Suzuki et al Chem Abstr vol. 116 Entry 235457g (1990).

*Primary Examiner*—John M. Ford
*Attorney, Agent, or Firm*—Keil & Weinkauf

[57] ABSTRACT

Quinoline-3-carboxamides I

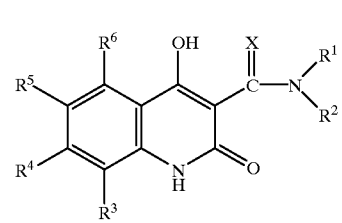

(I)

where $R^1$ is hydrogen, alkyl, alkenyl, alkynyl, cycloalkyl, and the organic radicals may be substituted or unsubstituted;

$R^2$ is hydrogen, hydroxyl, alkoxy, alkenyloxy, dialkylamino, alkyl, alkenyl, alkynyl, cycloalkyl, and the organic radicals may be substituted or unsubstituted;

or $R^1$, $R^2$ together denote an alkylene chain of 4 to 7 members and which may be interrupted by oxygen, sulfur or N-methyl;

$R^3$–$R^6$ are hydrogen, alkyl, alkoxy, haloalkyl, haloalkoxy, alkylthio, haloalkylthio, halogen, cyano or nitro;

X is oxygen or sulfur;

with the proviso that $R^2$ is not hydrogen, $C_1$–$C_3$-alkyl, n-butyl, 3-methylbutyl, cyclohexyl, hexyl, heptyl, octyl, 2-chlorobenzyl, 3-(dimethylamino)propyl, 3-(diethylamino)propyl, 2-morpholinoethyl or 2-(3,4-dimethoxyphenyl)ethyl when $R^1$ and $R^3$ to $R^6$ are hydrogen and X is oxygen, and that $R^2$ is not benzyl when $R^1$ is methyl, $R^3$ to $R^6$ are hydrogen and X is oxygen, and that $R^1$ and $R^2$ do not jointly denote morpholino when $R^3$ to $R^6$ are hydrogen and X is oxygen.

1 Claim, No Drawings

QUINOLINE-3-CARBOXAMIDES, THEIR MANUFACTURE AND USE

This is a Divisional of prior application Ser. No. 08/794,572, filed Feb. 3, 1997, now U.S. Pat. No. 5,798,451 which is an FWC of 08/542,136, Oct. 12, 1995 abandoned; which is an FWC of 08/241,390, May 11, 1994 abandoned; which is an FWC of 07/981,356, Nov. 25, 1992 abandoned.

The present invention relates to quinoline-3-carboxamides of the formula I

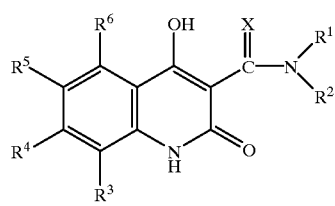

where the substituents have the following meanings:

$R^1$ hydrogen, $C_1$–$C_{25}$-alkyl, $C_3$–$C_{25}$-alkenyl, $C_3$–$C_{25}$-alkynl or $C_3$–$C_8$-cycloalkyl, where these groups may carry from one to five halogen atoms and/or from one to three of the following radicals: cyano, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, phenyl, phenylthio, phenoxy, and the phenyl radicals in turn may bear from one to three of the following groups: $C_1$–$C_4$-alkyl, $C_1$–$C_4$-alkoxy, $C_1$–$C_4$-haloalkyl, $C_1$–$C_4$-haloalkoxy, halogen, cyano or nitro;

$R^2$ hydrogen, hydroxyl, $C_1$–$C_8$-alkoxy, $C_3$–$C_8$-alkenyloxy, di-$C_1$–$C_4$-alkylamino, $C_1$–$C_{25}$-alkyl, $C_3$–$C_{25}$-alkenyl, $C_3$–$C_{25}$-alkynyl or $C_3$–$C_8$-cycloalkyl, where these groups may carry from one to five halogen atoms and/or from one to three of the following radicals: cyano, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, phenyl, phenylthio, phenoxy, and the phenyl radicals in turn may bear from one to three of the following groups: $C_1$–$C_4$-alkyl, $C_1$–$C_4$-alkoxy, $C_1$–$C_4$-haloalkyl, $C_1$–$C_4$-haloalkoxy, halogen, cyano or nitro;

$R^2$ further denotes substituted $C_1$–$C_8$-alkoxy, $C_3$–$C_8$-alkenyloxy, di-$C_1$–$C_4$-alkylamino, $C_1$–$C_{25}$-alkyl, $C_3$–$C_{25}$-alkenyl, $C_3$–$C_{25}$-alkynyl or $C_3$–$C_8$-cycloalkyl, where these groups are substituted by from one to five halogen atoms and/or by one or two 5- to 6-membered heterocyclic, aliphatic or aromatic radicals containing from one to three heteroatoms selected from the group consisting of oxygen, sulfur and nitrogen, and which radicals may bear one or two of the following substituents: halogen, $C_1$–$C_3$-alkyl or $C_1$–$C_3$-alkoxy;

or $R^1$, $R^2$ together denote an alkylene chain of 4 to 7 members and which may be interrupted by oxygen, sulfur or N-methyl;

$R^3$–$R^6$ hydrogen, $C_1$–$C_4$-alkyl, $C_1$–$C_4$-alkoxy, $C_1$–$C_4$-haloalkyl, $C_1$–$C_4$-haloalkoxy, $C_1$–$C_4$-alkylthio, $C_1$–$C_4$-haloalkylthio, halogen, cyano or nitro;

X oxygen or sulfur or environmentally tolerated salts thereof;

with the proviso that $R^2$ is not hydrogen, $C_1$–$C_3$-alkyl, n-butyl, 3-methylbutyl, cyclohexyl, hexyl, heptyl, octyl, 2-chlorobenzyl, 3-(dimethylamino)propyl, 3-(diethylamino)propyl, 2-morpholinoethyl or 2-(3,4-dimethoxyphenyl)ethyl when $R^1$ and $R^3$ to $R^6$ are hydrogen and X is oxygen, and with the proviso that $R^2$ is not benzyl when $R^1$ is methyl, $R^3$ to $R^6$ are hydrogen and X is oxygen, and further with the proviso that $R^1$ and $R^2$ do not together denote morpholino when $R^3$ to $R^6$ are hydrogen and X is oxygen.

The invention further relates to herbicidal agents containing compounds I as active ingredients, and the herbicidal use of quinoline-3-carboxamides of the formula I, including the compounds disclaimed in the disclaimer.

The compounds of the formula I may be present in the following tautomeric forms, which are also encompassed by the invention:

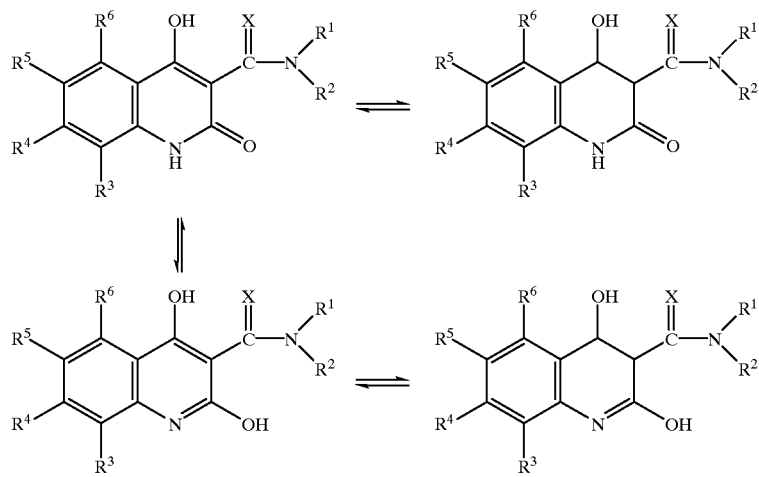

4-Hydroxycarbostyryls having anti-inflammatory and anti-allergic properties are known from Chemical Abstracts, Vol. 113, No. 211864z.

Quinoline-3-carboxamides having anticoagulant (Khim.-Farm. Zh., 24(4), 31 (Russ), 1990) and antibacterial (Chemical Abstracts 70, Nr. 67681x) properties, and derivatives acting as local anesthetics (Farm. Zh. (Kiev) (2), 78,1991), are also known.

The object of the present invention was to provide novel, herbicidally effective quinoline-3-carboxamides and methods of preparing them.

This object was achieved by the quinoline-3-carboxamides I, methods of preparing them and herbicidal agents containing the compounds I. Salts of the compounds I are also encompassed by the invention.

The quinoline-3-carboxamides I are obtained for example by reacting a quinoline-3-carboxylate of the formula IIa in conventional manner (Khim.-Farm. Zh., Vol. 24, issue 4, pp. 31 and 32 (Russ.)= pp. 257–259 (Engl.), 1990), in the presence or absence of an organic solvent, with a substituted amine of the formula III:

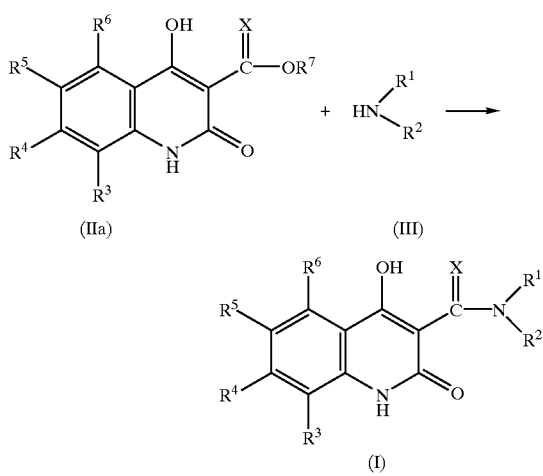

$R^7$ in formula IIa is a low-molecular-weight alkyl group, preferably $C_1$–$C_4$-alkyl such as methyl, ethyl, propyl, 1-methylethyl, butyl, 1-methylpropyl, 2-methylpropyl or 1,1-dimethylethyl.

The reaction is generally carried out at from 20° C. to 250° C., preferably 100° C. to 180° C., in an inert organic solvent.

Examples of suitable solvents or diluents are aliphatic, alicyclic and aromatic hydrocarbons, such as pentane, hexane, cyclohexane, benzene, toluene, and xylenes; ethers such as diethyl and di-n-butyl ether, methyl tert.-butyl ether, dimethoxyethane, ethylene glycol dimethyl ether, tetrahydrofuran and dioxane; alcohols such as methanol, ethanol, propanol and butanol; and aprotic dipolar solvents such as dimethylformamide, dimethyl sulfoxide and pyridine.

Mixtures of these substances may also be used as solvents and diluents.

The starting materials are generally reacted with each other in stoichiometric amounts. It may be advantageous, for instance to increase the yield, to use one of the starting materials, preferably the amine, in an excess of 0.1 to 10 mole equivalents.

The reaction is generally carried out at atmospheric pressure. However, it may be advantageous, depending on the type of amine employed, to carry out the reaction at superatmospheric pressure, especially autogenously increased pressure, in an autoclave.

The compounds I may also be obtained from quinoline-3-carboxylic acids IIb by first converting IIb in conventional manner into the halide or another active form of the carboxylic acid function, and then amidating this derivative with an amine III.

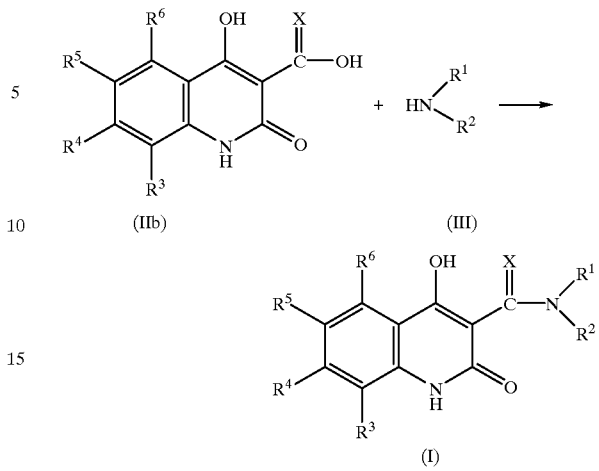

Examples of active forms of the carboxylic acids are, in addition to the halides (especially chlorides and bromides), imidazolides. Generally, the halides are preferred.

They are obtained by reacting the carboxylic acids IIb with a halogenating agent such as phosgene, thionyl chloride, phosphorus oxychloride, and phosphorus tri- and -pentachloride.

The subsequent amidation is carried out at from (–20) to 80° C., preferably from 0 to 30° C., in an inert organic solvent.

Suitable solvents for this reaction are, in particular, hydrocarbons such as benzene and toluene, halohydrocarbons such as dichloromethane, and ethers such as diethyl ether and tert-butyl methyl ether.

As hydrogen halide is formed on the amidation of acid halides, it is advantageous for increasing the yield to use the amine III in an excess, or to add an acid-binding agent such as triethylamine.

The quinoline-3-carboxamides I may advantageously be prepared from the carboxylic acids IIb in a single stage: the carboxylic acid IIb is reacted with an amine III in conventional manner (WO 90 15052) in the presence of a dehydrating agent, e.g., propanephosphonic anhydride or dicyclohexylcarbodiimide, at from 0 to 50° C., preferably 5 to 25° C., in an inert solvent such as dichloromethane, tetrahydrofuran, toluene or ethyl acetate.

Compounds of the formula I in which X is oxygen and $R^1$ is hydrogen may also be obtained in conventional manner (J. Org. Chem. Vol. 44, pp. 4877 et seq. (1979)) by reacting a 2,4-dihydroxyquinoline IV with an isocyanate of the formula V.

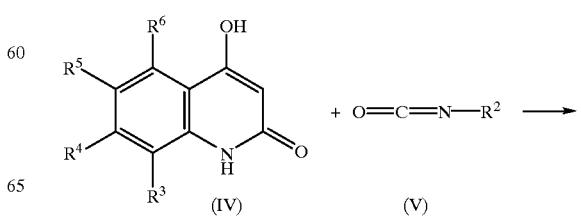

-continued

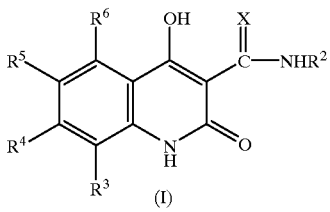

The quinoline-3-carboxylic acids and esters of the formula II are known or may be prepared by known methods (Australian J. Chem. Vol. 7, p. 348, p. 368 (1954)).

The 2,4-dihydroxyquinolines IV are also known or may be prepared by known methods, e.g., Monatsh. Chem., Vol. 96, 418 (1965).

The amines of the formula III and isocyanates of the formula V required for the reactions are either known or commercially available, or may be prepared by generally known chemical processes.

In view of the use to which the quinoline-3-carboxamides of the formula I are to be put, the following radicals are suitable substituents:

$R^1$ hydrogen, branched or straight-chain $C_1C_{25}$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl, 1-ethyl-2-methylpropyl, heptyl, 1-methylheptyl, octyl, nonyl, decyl, undecyl, dodecyl, tridecyl, tetradecyl, pentadecyl, hexadecyl, heptadecyl, octadecyl, nonadecyl, arachidyl, heneicosanyl, docosyl, tricosyl, tetracosyl and pentacosyl;

especially $C_1-C_{15}$-alkyl, for example $C_1-C_6$-alkyl, such as methyl, ethyl, 1-methylethyl, 1-methylpropyl, 2-methylpropyl, 1,1-dimethylethyl and 1,1-dimethylpropyl;

branched or straight-chain $C_3-C_{25}$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-buteyl, 1,2-dimethyl-3-butenyl, 1,3-dimethyl-2-butenyl, 1,3-diethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and ethyl-2-methyl-2-propenyl, 10-undecenyl, 9-tetradecenyl, 9-hexadecenyl, 6-octadecenyl, 9-octadecenyl, 11-octadecenyl, 9,12-octadecadienyl, 11-eicosenyl, 13-eicosenyl and 13-docosenyl;

especially $C_3-C_{15}$-alkenyl, for example $C_3-C_6$-alkenyl, such as 2-propenyl, 2-butenyl, 3-butenyl, 1-methyl-2-propenyl, 2-methyl-2-propenyl and 1-methyl-2-butenyl;

$C_3-C_{25}$-alkynyl, especially $C_3-C_{15}$-alkynyl, particularly preferably $C_3-C_8$-alkynyl, e.g., propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

$C_3-C_8$-cycloalkyl, such as cyclopropyl, cyclobutyl, cyclopentyl, cyclohexyl, cycloheptyl and cyclooctyl, especially cyclopropyl and cyclohexyl;

the abovementioned organic groups may bear from one to five halogen atoms, such as fluorine, chlorine, bromine and iodine, preferably fluorine, chlorine and bromine, and especially fluorine and chlorine, and/or from one to three of the following radicals:

cyano;

$C_3-C_8$-cycloalkyl, such as cyclopropyl, cyclobutyl, cyclopentyl, cyclohexyl, cycloheptyl and cyclooctyl, especially cyclopropyl and cyclohexyl;

$C_1-C_4$-alkoxy, such as methoxy, ethoxy, n-propoxy, 2-methylethoxy, n-butoxy, 1-methylpropoxy, 2-methylpropoxy and 1,1-dimethylethoxy, especially methoxy and ethoxy;

$C_1-C_4$-haloalkoxy, such as chloromethoxy, dichloromethoxy, trichloromethoxy, fluoromethoxy, difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, especially 2,2,2-trifluoroethyloxy and 2-chloro-2,2-difluoroethoxy;

$C_1-C_4$-alkylthio, such as methylthio, ethylthio, n-propylthio, 1-methylethylthio, n-butylthio, 1-methylpropylthio, 2-methylpropylthio and 1,1-dimethylethylthio, especially methylthio;

$C_1-C_4$-haloalkylthio, such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chlor-2,2-difluoroethylthio, 2,2-dichloro-2-fluoroethylthio, 2,2,2-trichloroethylthio and pentafluoroethylthio, especially trichloromethylthio;

phenyl, phenylthio, phenoxy, where the phenyl radicals in turn may bear from one to five halogen atoms such as fluorine, chlorine, bromine and iodine, especially fluorine and chlorine, and/or from one to three of the following groups:

cyano or nitro;

$C_1-C_4$-alkyl, as mentioned above, especially methyl, ethyl, propyl, 1-methylpropyl and 1,1-dimethylpropyl;

$C_1-C_4$-alkoxy, as mentioned above, especially methoxy and ethoxy;

$C_1-C_4$-haloalkyl, as mentioned above, especially trifluoromethyl;

$C_1-C_4$-haloalkoxy, as mentioned above, especially trifluoromethoxy;

$R^2$ hydrogen, hydroxy;

$C_1-C_8$-alkoxy, e.g., methoxy, ethoxy, n-propoxy, 2-methylethoxy, n-butoxy, 1-methylpropoxy, 2-methylpropoxy and 1,1-dimethylethoxy, especially $C_1-C_4$-alkoxy such as methoxy, ethoxy, propoxy, butoxy;

$C_3-C_8$-alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 3-methyl-2-butenyloxy, 1-methyl-2-butenyloxy, 2-methyl- 2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-4-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-4-butenyl, 1-ethyl-2-butenyl, 1-ethyl-3-butenyl, 2-ethyl-2-butenyloxy, 2-ethyl-3-butenyloxy, 1,1,2-trimethyl-2-propenyloxy, 1-ethyl-1-methyl-2-propenyloxy and ethyl-2-methyl-2-propenyloxy, especially 2-propenyloxy;

di-$C_1$–$C_4$-alkylamino, $C_1$–$C_{25}$-alkyl, $C_3$–$C_{25}$-alkenyl and -alkynyl and $C_3$–$C_8$-cycloalkyl, as mentioned above generally and particularly for $R^1$, and the abovementioned organic groups may bear from one to five halogen atoms such as fluorine, chlorine, bromine and iodine, preferably fluorine, chlorine and bromine, and especially fluorine and chlorine, and/or from one to three of the following radicals:
cyano,
$C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio and di-$C_1$–$C_4$-alkylamino, each as mentioned individually above, phenyl, phenylthio, phenoxy, and the phenyl radicals in turn may bear from one to five halogen atoms such as fluorine, chlorine, bromine and iodine, especially fluorine and chlorine, and/or from one to three of the following groups:
cyano or nitro,
$C_1$–$C_4$-alkyl, $C_1$–$C_4$-alkoxy, $C_1$–$C_4$-haloalkyl and $C_1$–$C_4$-haloalkoxy, each as mentioned above;

$R^2$ may further denote substituted $C_1$–$C_8$-alkoxy, $C_3$–$C_8$-alkenyloxy, di-$C_1$–$C_4$-alkylamino, $C_1$–$C_{25}$-alkyl, $C_3$–$C_{25}$-alkenyl, $C_3$–$C_{25}$-alkynyl or $C_3$–$C_8$-cycloalkyl, and these groups are substituted by from one to five halogen atoms and/or one or two 5- or 6-membered heterocyclic, aliphatic or aromatic radicals containing one to three heteroatoms selected from the group consisting of oxygen, sulfur and nitrogen; the following heterocyclic radicals are given by way of example: 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrrolyl, 3-pyrazolyl, 4-pyrazolyl, 5-pyrazolyl, 2-pyridyl, 4-pyridyl, 4-pyridyl, oxa-2,4-diazolyl, oxa-3,4-diazolyl, thia-2,4-diazolyl, thia-3,4-diazolyl and triazolyl;

and these heterocyclic radicals may bear one or two of the following substituents:
halogen, such as fluorine, chlorine, bromine and iodine, especially fluorine and chlorine, $C_1$–$C_3$-alkyl or $C_1$–$C_3$-alkoxy, as mentioned above;

$R^1$ and $R^2$ together denote a $C_4$–$C_7$-alkylene chain which may be interrupted by oxygen, sulfur or N-methyl, such as —(CH—)$_3$—, —(CH$_2$)$_4$—, —(CH$_2$)$_5$—, —(CH$_2$)$_6$—, —CH$_2$—O—CH$_2$—, —CH$_2$—CH$_2$—O—CH$_2$—CH$_2$—, —CH$_2$—S—CH$_2$—, —CH$_2$—CH$_2$—S—CH$_2$—CH$_2$—, —CH$_2$—N(CH$_3$)—CH$_2$—CH$_2$—, especially —(CH$_2$)$_5$— and —CH$_2$—CH$_2$—O—CH$_2$—CH$_2$—;

$R^3$ to $R^6$
hydrogen;
halogen, such as fluorine, chlorine, bromine and iodine, especially fluorine and chlorine;
cyano or nitro;
$C_1$–$C_4$-alkyl, $C_1$–$C_4$-alkoxy, $C_1$–$C_4$-haloalkyl, $C_1$–$C_4$-haloalkoxy, $C_1$–$C_4$-alkylthio or $C_1$–$C_4$-haloalkylthio, each as mentioned above individually for $R^1$.

Examples of suitable salts of compounds I are agriculturally useful salts such as alkali metal salts, especially the potassium and sodium salts, alkaline earth metal salts, especially the calcium, magnesium and barium salts, manganese, copper, zinc or iron salts, and ammonium, phosphonium, tetraalkylammonium salts, benzyltrialkylammonium salts, trialkylsulfonium salts and trialkylsulfoxonium salts.

Examples of particularly preferred compounds of the formula I are given in the following table:

TABLE

Compounds of the structure I

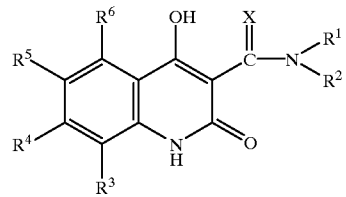

| $R^1$ | $R^2$ | $R^3$ | $R^4$ | $R^5$ | $R^6$ | X |
|---|---|---|---|---|---|---|
| H | 1,1-dimethyl-2-propenyl | H | H | H | H | O |
| H | 2-propynyl | H | H | H | H | O |
| H | 1-methyl-2-propynyl | H | H | H | H | O |
| H | 1,1-dimethyl-2-propynyl | H | H | H | H | O |
| H | benzyl | H | H | H | H | O |
| H | 1-methyl-phenylmethyl | H | H | H | H | O |
| H | 1,1-dimethyl-phenylmethyl | H | H | H | H | O |
| H | 2-phenylethyl | H | H | H | H | O |
| H | 2-methyl-thioethyl | H | H | H | H | O |
| H | 1-methyl-2-methylthioethyl | H | H | H | H | O |
| H | 1,1-dimethyl-2-methylthioethyl | H | H | H | H | O |
| H | 2-fluoroethyl | H | H | H | H | O |
| H | 2-fluoro-1-methylethyl | H | H | H | H | O |
| H | 1,1-dimethyl-2-fluoroethyl | H | H | H | H | O |
| H | 2-chloroethyl | H | H | H | H | O |
| H | 2-chloro-1-methyl-ethyl | H | H | H | H | O |
| H | 2-chloro-1,1-dimethylethyl | H | H | H | H | O |
| H | 2-cyanoethyl | H | H | H | H | O |
| H | 2-cyano-1,1-dimethylethyl | H | H | H | H | O |
| H | dimethylamino | H | H | H | H | O |
| H | 2-chlorobenzyl | H | H | H | H | O |
| H | 4-methoxy-benzyl | H | H | H | H | O |
| H | OH | H | H | H | H | O |
| H | methoxy | H | H | H | H | O |
| H | ethoxy | H | H | H | H | O |

TABLE-continued

Compounds of the structure I

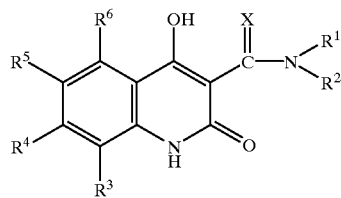

| R¹ | R² | R³ | R⁴ | R⁵ | R⁶ | X |
|---|---|---|---|---|---|---|
| H | propoxy | H | H | H | H | O |
| H | 2-propenyloxy | H | H | H | H | O |
| H | benzyloxy | H | H | H | H | O |
| H | 2-phenoxyethyl | H | H | H | H | O |
| H | H | H | Cl | H | H | O |
| H | H | H | H | H | Cl | O |
| H | H | H | methyl | H | H | O |
| H | H | H | methoxy | H | H | O |
| H | H | H | $NO_2$ | H | H | O |
| H | H | H | cyano | H | H | O |
| H | tert.butyl | F | H | H | H | O |
| H | tert.butyl | H | F | H | H | O |
| H | tert.butyl | H | H | F | H | O |
| H | tert.butyl | H | H | H | F | O |
| H | isopropyl | H | H | F | H | O |
| H | isopropyl | H | F | H | H | O |
| H | isopropyl | F | H | H | H | O |
| H | tert.butyl | methyl | H | H | H | O |
| H | isopropyl | methyl | H | H | H | O |
| H | tert.butyl | H | methyl | H | H | O |
| H | isopropyl | H | methyl | H | H | O |
| H | tert.butyl | H | H | methyl | H | O |
| H | isopropyl | H | H | methyl | H | O |
| H | tert.butyl | H | methoxy | methoxy | H | O |
| H | tert.butyl | $NO_2$ | H | $NO_2$ | H | O |
| H | isopropyl | $NO_2$ | H | $NO_2$ | H | O |
| H | tert.butyl | methyl | H | Br | H | O |
| H | tert.butyl | H | 1,1,2,2-tetrafluoroethoxy | H | H | O |
| H | tert.butyl | Cl | H | H | H | O |
| H | isopropyl | Cl | H | H | H | O |
| H | tert.butyl | methoxy | methoxy | methoxy | H | O |
| H | tert.butyl | methyl | Cl | H | H | O |
| H | tert.butyl | H | NO2 | H | H | O |
| H | tert.butyl | Br | H | Br | H | O |
| H | tert.butyl | H | H | methoxy | H | O |
| H | tert.butyl | methyl | methyl | Br | H | O |
| H | tert.butyl | $NO_2$ | H | methyl | H | O |
| H | tert.butyl | H | H | trifluoromethyl | H | O |
| H | tert.butyl | Cl | H | Cl | H | O |
| H | isopropyl | Cl | H | Cl | H | O |
| methyl | methyl | H | H | H | H | O |
| methyl | isopropyl | H | H | H | H | O |
| methyl | ethyl | H | H | H | H | O |
| methyl | Cyclopropyl | H | H | H | H | O |
| Benzyl | benzyl | H | H | H | H |   |
| H | methyl | H | Cl | H | H | O |
| H | ethyl | H | Cl | H | H | O |
| H | propyl | H | Cl | H | H | O |
| H | 2,2-dimethylbutyl | H | H | H | H | O |
| H | 1,1-dimethylbutyl | H | H | H | H | O |
| H | 1,1-dimethylpentyl | H | H | H | H | O |
| H | cyclohexyl | H | H | H | H | O |
| H | cyclopentyl | H | H | H | H | O |
| H | 1,2,2,-trimethylpropyl | H | H | H | H | O |
| H | 1-methylcyclopropyl | H | H | H | H | O |
| H | cyclopropylmethyl | H | H | H | H | O |
| H | 1-(cyclopropyl)-ethyl | H | H | H | H | O |
| H | 1-methylcyclohexyl | H | H | H | H | O |
| H | cyclohexylmethyl | H | H | H | H | O |
| H | 2-propenyl | H | H | H | H | O |
| H | 1-methyl-2-propenyl | H | H | H | H | O |
| H | 1,1-dimethyl-2-propenyl | H | H | H | H | S |
| H | 2-propynyl | H | H | H | H | S |
| H | 1-methyl-2-propynyl | H | H | H | H | S |
| H | 1,1-dimethyl-2-propynyl | H | H | H | H | S |
| H | benzyl | H | H | H | H | S |
| H | 1-methylphenylmethyl | H | H | H | H | S |
| H | 1,1-dimethylphenylmethyl | H | H | H | H | S |
| H | 2-phenylethyl | H | H | H | H | S |
| H | 2-methylthioethyl | H | H | H | H | S |
| H | 1-methyl-2-methylthioethyl | H | H | H | H | S |
| H | 1,1-dimethyl-2-methylthioethyl | H | H | H | H | S |
| H | 2-fluoroethyl | H | H | H | H | S |
| H | 2-fluoro-1-methylethyl | H | H | H | H | S |
| H | 1,1-dimethyl-2-fluoroethyl | H | H | H | H | S |
| H | 2-chlorothyl | H | H | H | H | S |
| H | 2-chloro-1-methylethyl | H | H | H | H | S |
| H | 2-chloro-1,1-dimethylethyl | H | H | H | H | S |
| H | 2-cyanoethyl | H | H | H | H | S |
| H | 2-cyano-1,1-dimethylethyl | H | H | H | H | S |
| H | dimethylamino | H | H | H | H | S |
| H | 2-chlorobenzyl | H | H | H | H | S |
| H | 4-methoxybenzyl | H | H | H | H | S |
| H | OH | H | H | H | H | S |
| H | methoxy | H | H | H | H | S |
| H | ethoxy | H | H | H | H | S |
| H | propoxy | H | H | H | H | S |
| H | 2-propenyloxy | H | H | H | H | S |
| H | benzyloxy | H | H | H | H | S |
| H | 2-phenoxyethyl | H | H | H | H | S |
| H | H | H | Cl | H | H | S |
| H | H | H | H | H | Cl | S |
| H | H | H | methyl | H | H | S |
| H | H | H | methoxy | H | H | S |
| H | H | H | $NO_2$ | H | H | S |
| H | H | H | cyano | H | H | S |
| H | tert.butyl | F | H | H | H | S |
| H | tert.butyl | H | F | H | H | S |
| H | tert.butyl | H | H | F | H | S |
| H | tert.butyl | H | H | H | F | S |

TABLE-continued

Compounds of the structure I $$\text{structure with } R^6, OH, X, R^5, R^1, R^2, R^4, R^3, NH, O$$

| R¹ | R² | R³ | R⁴ | R⁵ | R⁶ | X |
|---|---|---|---|---|---|---|
| H | isopropyl | H | H | H | F | S |
| H | isopropyl | H | H | F | H | S |
| H | isopropyl | H | F | H | H | S |
| H | isopropyl | F | H | H | H | S |
| H | tert.butyl | methyl | H | H | H | S |
| H | isopropyl | methyl | H | H | H | S |
| H | tert.butyl | H | methyl | H | H | S |
| H | isopropyl | H | methyl | H | H | S |
| H | tert.butyl | H | H | methyl | H | S |
| H | isopropyl | H | H | methyl | H | S |
| H | tert.butyl | H | methoxy | methoxy | H | S |
| H | tert.butyl | NO₂ | H | NO₂ | H | S |
| H | isopropyl | NO₂ | H | NO₂ | H | S |
| H | tert.bButyl | methyl | H | Br | H | S |
| H | tert.butyl | H | 1,1,2,2-tetra-fluoroethoxy | H | H | S |
| H | tert.butyl | Cl | H | H | H | S |
| H | isopropyl | Cl | H | H | H | S |
| H | tert.butyl | methoxy | methoxy | methoxy | H | S |
| H | tert.butyl | methyl | Cl | H | H | S |
| H | tert.butyl | H | NO2 | H | H | S |
| H | tert.butyl | Br | H | Br | H | S |
| H | tert.butyl | H | Cl | H | H | S |
| H | tert.butyl | H | H | methoxy | H | S |
| H | tert.butyl | methyl | methyl | Br | H | S |
| H | tert.butyl | NO₂ | H | methyl | H | S |
| H | tert.butyl | H | H | trifluoro-methyl | H | S |
| H | tert.butyl | Cl | H | Cl | H | S |
| H | isopropyl | Cl | H | Cl | H | S |
| methyl | methyl | H | H | H | H | S |
| methyl | isopropyl | H | H | H | H | S |
| methyl | ethyl | H | H | H | H | S |
| methyl | cyclopropyl | H | H | H | H | S |
| benzyl | benzyl | H | H | H | H | S |
| H | methyl | H | Cl | H | H | S |
| H | ethyl | H | Cl | H | H | S |
| H | propyl | H | Cl | H | H | S |
| H | 2,2-dimethyl-butyl | H | H | H | H | S |
| H | 1,1-dimethyl-butyl | H | H | H | H | S |
| H | 1,1-dimethyl-pentyl | H | H | H | H | S |
| H | cyclohexyl | H | H | H | H | S |
| H | cyclopentyl | H | H | H | H | S |
| H | 1,2,2-tri-methylpropyl | H | H | H | H | S |
| H | 1-methyl-cyclopropyl | H | H | H | H | S |
| H | cyclopropyl-methyl | H | H | H | H | S |
| H | 1-(cyclo-propyl)-ethyl | H | H | H | H | S |
| H | 1-methyl-cyclohexyl | H | H | H | H | S |
| H | cyclohexyl-methyl | H | H | H | H | S |
| H | 2-propenyl | H | H | H | H | S |
| H | 1-methyl-2-propenyl | H | H | H | H | S |

The compounds I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalene-sulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.01 to 95, and preferably 0.5 to 90, % by weight of active ingredient. The active ingredients are used in a purity of from 90 to 100, and preferably from 95 to 100, % (according to the NMR spectrum).

The compounds I according to the invention may be formulated for example as follows:

I. 90 parts by weight of compound no. 1.01 is mixed with 10 parts by weight of N-methyl-α-pyrrolidone. A mixture is obtained which is suitable for application in the form of very fine drops.

II. 20 parts by weight of compound no. 1.05 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.01 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.05 is dissolved in a mixture consisting of 25 parts by weight of cyclohexanone, 65 parts by weight of a mineral oil fraction having a boiling point between 210 and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.01 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.01 is intimately mixed with 97 parts by weight of particulate kaolin. A dust is obtained containing 3% by weight of the active ingredient.

VII. 30 parts by weight of compound no. 1.01 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.01 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3, preferably 0.01 to 1, kg of active ingredient per hectare.

In view of the numerous application methods possible, the compounds according to the invention, or agents containing them, may be used in a large number of crops. Those which follow are given by way of example:

| | |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissirvia* | sugarbeets |
| *Beta vulgaris* spp. *rapa* | fodder beets |
| *Brassica napus* var. *napus* | rapeseed |
| *Brassica napus* var. *napobrassica* | swedes |
| *Camellia sinensis* | tea plants |
| *Carthamus tinctorius* | safflower |
| *Carya illinoinensis* | pecan trees |
| *Citrus limon* | lemons |
| *Citrus sinensis* | orange trees |
| *Coffea arabica (Coffea canephora, Coffea liberica)* | coffee plants |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum (Gossypium arboreum, Gossypium herbaceum, Gossypium vitifolium)* | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Musa* spp. | banana plants |
| *Nicotiana tabacum (N. rustica)* | tobacco |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus* spp. | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ricinus communis* | castor-oil plants |
| *Saccharum officinarum* | sugar cane |
| *Secale cereale* | rye |
| *Solanum tuberosum* | Irish potatoes |
| *Sorghum bicolor (s. vulgare)* | sorghum |
| *Theobroma cacao* | cacao plants |
| *Trifolium pratense* | red clover |
| *Triticum aestivum* | wheat |
| *Triticum durum* | wheat |
| *Vicia faba* | tick beans |
| *Vitis vinifera* | grapes |

| | |
|---|---|
| *Zea mays* | Indian corn, sweet corn, maize |

To increase the spectrum of action and to achieve synergistic effects, the auinoline-3-carboxamides I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, sulfonylureas, (hetero)-aryloxyphenoxypropionic acids and salts, esters, amides thereof, etc.

It may also be useful to apply the novel compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

Synthesis examples

EXAMPLE 1

Preparation of 4-hydroxy-2-oxoquinoline-3-carboxylic acid tert-butylamide 8.76 g (0.04 mol) of methyl 4-hydroxy-2-oxoquinoline-3-carboxylate was stirred with 3.7 g (0.05 mol) of tert-butylamine in 60 ml of ethanol in a miniautoclave for 8 hours at 150° C. under autogenous pressure. After cooling, the crystals were removed by suction filtration, washed with ligroin and dried.

M.p.: 230–231° C.; yield: 7.7 g (74% of theory).

Further compounds I were prepared analogously with appropriate modifications of the starting materials. The compounds thus obtained are listed with their physical data in Table 1 below.

TABLE 1

Quinoline-3-carboxamides of the structure I; X = O

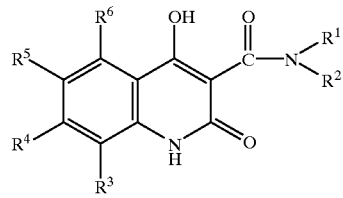

(I)

| No. | $R^1$ | $R^2$ | $R^3$ | $R^4$ | $R^5$ | $R^6$ | Phys. data m.p. ° C. |
|---|---|---|---|---|---|---|---|
| 1.01 | H | tert.-butyl | H | H | H | H | 230 |
| 1.02 | H | isopropyl | H | H | H | H | 243 |
| 1.03 | H | 1-methylpropyl | H | H | H | H | 206 |
| 1.04 | H | 2-methylpropyl | H | H | H | H | 225 |
| 1.05 | H | 1-ethylpropyl | H | H | H | H | 205 |
| 1.06 | H | 1,1,2-trimethylpropyl | H | H | H | H | 269–270 |
| 1.07 | H | 2-methoxy-1-methylethyl | H | H | H | H | 200 |
| 1.08 | H | 2-methoxy-1-ethylethyl | H | H | H | H | 168–170 |
| 1.09 | H | 1-ethyl-1-methylpentyl | H | H | H | H | 148–150 |
| 1.10 | H | 2-methylbutyl | H | H | H | H | 177–180 |
| 1.11 | H | n-heptyl | H | H | H | H | 150 |
| 1.12 | H | n-octyl | H | H | H | H | 146 |
| 1.13 | H | n-nonyl | H | H | H | H | 147 |
| 1.14 | H | n-decyl | H | H | H | H | 152 |
| 1.15 | H | n-undecyl | H | H | H | H | 138 |
| 1.16 | H | n-dodecyl | H | H | H | H | 130 |
| 1.17 | H | n-tridecyl | H | H | H | H | 132 |
| 1.18 | H | n-tetradecyl | H | H | H | H | 118 |
| 1.19 | H | n-pentadecyl | H | H | H | H | 120 |
| 1.20 | H | cyclopropyl | H | H | H | H | 270 |
| 1.21 | H | tert.-butyl | H | Cl | H | H | 295–298 |
| 1.22 | H | isopropyl | H | Cl | H | H | 305–310 |
| 1.23 | H | tert.-butyl | H | H | H | Cl | 287–291 |
| 1.24 | H | isopropyl | H | H | H | Cl | 280–285 |
| 1.25 | H | tert.-butyl | methyl | H | H | H | >220 |
| 1.26 | H | isopropyl | methyl | H | H | H | >220 |
| 1.27 | H | vyclopropyl | methyl | H | H | H | >220 |
| 1.28 | H | 1,1-dimethylpropynyl | methyl | H | H | H | 255 |
| 1.29 | H | 1-cyclopropylethyl | methyl | H | H | H | 269 |
| 1.30 | H | 1,1-dimethylpropenyl | methyl | H | H | H | 238 |
| 1.31 | H | 1-(methoxymethyl)-ethyl | methyl | H | H | H | 213 |
| 1.32 | H | tert.-butyl | H | H | H | F | 303 |
| 1.33 | H | isopropyl | H | H | H | F | 292 |
| 1.34 | H | cyclopropyl | H | H | H | F | 305 |
| 1.35 | H | 1,1-dimethylpropenyl | H | H | H | F | 265 |
| 1.36 | H | 1-cyclopropylethyl | H | H | H | F | 204 |

TABLE 1-continued

Quinoline-3-carboxamides of the structure I; X = O

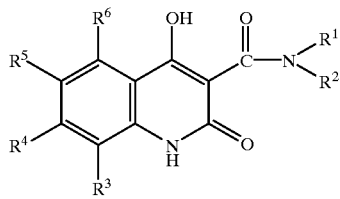

(I)

| No. | R¹ | R² | R³ | R⁴ | R⁵ | R⁶ | Phys. data m.p. °C. |
|---|---|---|---|---|---|---|---|
| 1.37 | H | 1-(methoxymethyl)-ethyl | H | H | H | F | 235 |
| 1.38 | H | tert.-butyl | H | F | H | H | 280 |
| 1.39 | H | isopropyl | H | F | H | H | 295 |
| 1.40 | H | cyclopropyl | H | F | H | H | 312 |
| 1.41 | H | 1-(methoxymethyl)-ethyl | H | F | H | H | 226 |
| 1.42 | H | 1,1-dimethylpropenyl | H | F | H | H | 261 |
| 1.43 | H | 1-cyclopropylethyl | H | F | H | H | 257 |
| 1.44 | H | tert.-butyl | H | H | H | methyl | 258 |
| 1.45 | H | isopropyl | H | H | H | methyl | 275 |
| 1.46 | H | tert.-butyl | H | methoxy | methoxy | H | 337 |
| 1.47 | H | cyclopropyl | H | H | H | methyl | 266 |
| 1.48 | H | 1-(methoxymethyl)-ethyl | H | H | H | methyl | 173–175 |
| 1.49 | H | tert.-butyl | methyl | H | H | methyl | 222–224 |
| 1.50 | H | isopropyl | methyl | H | H | methyl | 251–254 |
| 1.51 | H | tert.-butyl | H | H | F | H | 273–277 |
| 1.52 | H | isopropyl | H | H | F | H | 274–280 |
| 1.53 | H | tert.-butyl | H | methyl | H | H | 287–292 |
| 1.54 | H | cyclopropyl | H | H | F | H | 306–311 |
| 1.55 | H | isopropyl | H | methyl | H | H | 248–255 |
| 1.56 | H | 1-(methoxymethyl)-ethyl | H | H | F | H | 214–216 |
| 1.57 | H | cyclopropyl | H | methyl | H | H | 289–293 |
| 1.58 | H | 1,1-dimethylpropenyl | H | H | F | H | 243–248 |
| 1.59 | H | 1-(methoxymethyl)-ethyl | H | methyl | H | H | 204–207 |
| 1.60 | H | 1-cyclopropylethyl | H | H | F | H | 213–221 |
| 1.61 | H | 1,1-dimethylpropenyl | H | methyl | H | H | 265–271 |
| 1.62 | H | 1,1-dimethylpropenyl | H | H | H | methyl | 230–234 |
| 1.63 | H | 1-cyclopropylethyl | H | methyl | H | H | 258–262 |
| 1.64 | H | 1-cyclopropylethyl | H | H | H | methyl | 180–185 |
| 1.65 | H | tert.-butyl | H | H | Cl | H | 303–308 |
| 1.66 | H | isopropyl | H | H | Cl | H | 285–292 |
| 1.67 | H | cyclopropyl | H | H | Cl | H | 221–227 |
| 1.68 | H | 1-cyclopropylethyl | H | H | Cl | H | 269–272 |
| 1.69 | H | 1-(methoxymethyl)-ethyl | H | H | Cl | H | 222–228 |
| 1.70 | H | 1,1-dimethylpropenyl | H | H | Cl | H | 294–300 |
| 1.71 | H | tert.-butyl | H | H | Br | H | 312–316 |
| 1.72 | H | isopropyl | H | H | Br | H | 278–282 |
| 1.73 | H | cyclopropyl | H | H | Br | H | 304–309 |
| 1.74 | H | tert.-butyl | H | H | methyl | H | 269–275 |
| 1.75 | H | isopropyl | H | H | methyl | H | 242–247 |
| 1.76 | H | cyclopropyl | H | H | methyl | H | 297–305 |
| 1.77 | H | 1-cyclopropylethyl | H | H | methyl | H | 235–240 |
| 1.78 | H | 1-(methoxymethyl)-ethyl | H | H | methyl | H | 201–206 |
| 1.79 | H | 1,1-dimethylpropenyl | H | H | methyl | H | 256–260 |
| 1.80 | H | 1,1-dimethylethyl | H | H | Br | H | 279–282 |
| 1.81 | H | 1-(methoxymethyl)-ethyl | H | H | Br | H | 228–231 |
| 1.82 | H | 1,1-dimethylpropenyl | H | H | Br | H | 299–305 |
| 1.83 | H | tert.-butyl | H | H | methoxy | H | 288–292 |
| 1.84 | H | isopropyl | H | H | methoxy | H | 278–284 |
| 1.85 | H | 1-cyclopropylethyl | H | H | methoxy | H | 269–275 |
| 1.86 | H | 1-(methoxymethyl)-ethyl | H | H | methoxy | H | 236–241 |
| 1.87 | H | 1-(3-thienyl)-ethyl | H | H | H | F | 253–258 |
| 1.88 | H | 1-phenylethyl | H | H | H | F | 240–245 |
| 1.89 | H | tert.-butyl | Cl | H | Cl | H | 259–266 |
| 1.90 | H | isopropyl | Cl | H | Cl | H | 250–256 |
| 1.91 | H | 1-cyclopropylethyl | Cl | H | Cl | H | 237–241 |
| 1.92 | H | 1-(methoxymethyl)-ethyl | Cl | H | Cl | H | 185–190 |
| 1.93 | H | tert.-butyl | H | H | I | H | 296–302 |
| 1.94 | H | 1-cyclopropylethyl | H | H | I | H | 265–270 |
| 1.95 | H | 1-(methoxymethyl)-ethyl | H | H | I | H | 249–255 |
| 1.96 | H | isopropyl | H | H | I | H | 289–294 |

EXAMPLE 2

Preparation of 5-fluoro-4-hydroxy-2-oxoquinoline-3-carboxylic acid-tert.-butylamide, Na salt 6.0 g (0.023 mol) of 5-fluoro-4-hydroxy-2-oxoquinoline-3-carboxylic acid-tert.-butylamide is suspended methanol, and a solution of 1.25 g of sodium methylate in methanol is added. The solution is stirred for 1 hour at room temperature and then evaporated down, and the residue is dried.

M.p.: >399° C.; yield: 6.4 g, (98% of theory)

Further salts of compounds I were prepared with appropriate modification of the starting materials. The salts thus obtained are listed with their physical data in Table 2 below.

TABLE 2

Salts of compounds of the structure I

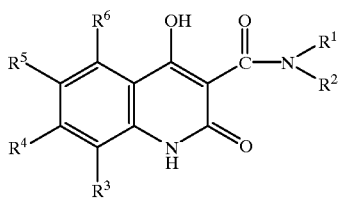

(I)

| No. | $R^1$ | $R^2$ | $R^3$ | $R^4$ | $R^5$ | $R^6$ | Counterion | Phys. data m.p. ° C. |
|---|---|---|---|---|---|---|---|---|
| 2.01 | H | tert.-butyl | H | H | H | F | $Na^+$ | 287–297 |
| 2.02 | H | tert.-butyl | H | H | H | H | $K^+$ | 332–337 |
| 2.03 | H | 1-cyclopropylethyl | H | H | H | F | $K^+$ | 290–295 |
| 2.04 | H | 1-cyclopropylethyl | H | H | H | F | $Na^+$ | 280–297 |
| 2.05 | H | tert.-butyl | H | H | H | H | $Na^+$ | 295–300 |
| 2.06 | H | tert.-butyl | H | H | H | H | $K^+$ | 289–296 |
| 2.07 | H | tert.-butyl | H | H | H | H | $N(CH_3)_4^+$ | $^1$H-NMR (DMSO) δ: 11.13(s, 1H), 9.98(s, 1H), 7.80(d, 1H), 7.29(t, 1H), 7.06(d, 1H), 6.92(t, 1H), 3.21(s, 12H), 1.35(s, 9H) |
| 2.08 | H | tert.-butyl | H | H | H | H | $N(C_2H_5)_4^+$ | $^1$H-NMR (DMSO) δ: 11.12(s, 1H), 9.98(s, 1H), 7.81(d, 1H), 7.29(t, 1H), 7.06(d, 1H), 6.95(t, 1H), 3.23(q, 6H); 1.35(s, 9H), 1.15(t, 10H) |
| 2.09 | H | tert.-butyl | H | H | H | H | $N(n-C_4H_9)_4^+$ | $^1$H NMR (DMSO) δ: 11.10(s, 1H), 9.98(s, 1H), 7.90(d, 1H), 7.31(t, 1H), 7.08(d, 1H), 6.95(t, 1H), 3.18(m, 8H), 1.55(m, 8H), 1.35(s, 9H), 1.28(m, 8H), 0.95(t, 12H) |

EXAMPLE 3

The quinoline-3-carboxylates as intermediates for the synthesis of the corresponding amides were prepared as disclosed in Australian Journal of Chem. Vol. 7, p. 348 and 368 (1954).

Selected examples are given in Table 3.

TABLE 3

Intermediates of the formula

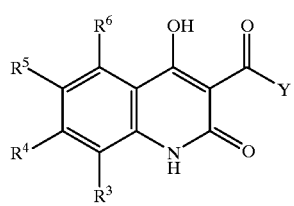

(II)

| No. | Y | $R^3$ | $R^4$ | $R^5$ | $R^6$ | Phys. data m.p. ° C. |
|---|---|---|---|---|---|---|
| 3.01 | methoxy | H | H | H | F | >399 |
| 3.02 | methoxy | H | F | H | H | 245 |
| 3.03 | methoxy | H | H | H | methyl | 250 |
| 3.04 | methoxy | H | methyl | H | H | 235 |
| 3.05 | methoxy | H | H | F | H | 271–274 |
| 3.06 | methoxy | H | H | Cl | H | 255–259 |

TABLE 3-continued

Intermediates of the formula (II)

[Structure II: quinoline with R6, OH, R5, R4, R3, and C(=O)Y substituents]

| No. | Y | $R^3$ | $R^4$ | $R^5$ | $R^6$ | Phys. data m.p. ° C. |
|---|---|---|---|---|---|---|
| 3.07 | methoxy | H | H | Br | H | 257–261 |
| 3.08 | methoxy | H | H | methyl | H | 236–244 |
| 3.09 | methoxy | H | methoxy | methoxy | H | 329–334 |
| 3.10 | methoxy | H | H | methoxy | H | 229–237 |
| 3.12 | methoxy | methyl | H | H | methyl | 252–255 |
| 3.12 | methoxy | H | H | I | H | >399 |

Use examples

The herbicidal action of compounds I is demonstrated in greenhouse experiments:

The vessels employed were plastic flowerpots filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rate for postemergence treatment was 3 kg/ha.

The pots were set up in the greenhouse at temperatures specific to their species—at from 20 to 350° C., or from 10 to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were Echinochboa crus-galli and Centaurea cyanus.

Compounds 1.01 and 1.05, applied postemergence at a rate of 3 kg/ha, have a very good herbicidal action.

We claim:

1. A method of combating the growth of unwanted plants, wherein the unwanted plants and/or their habitat are treated with a herbicidally effective amount of a quinoline-3-carboxamide of the formula I

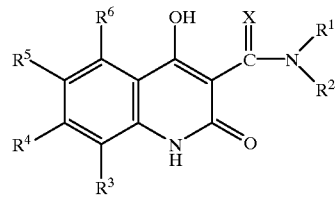

(I)

where $R^1$ is hydrogen, $C_1$–$C_{25}$-alkyl, $C_3$–$C_{25}$-alkenyl, $C_3$–$C_{25}$-alkynyl or $C_3$–$C_8$-cycloalkyl, where these groups may carry from one to five halogen atoms and/or from one to three of the following radicals: cyano, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, phenyl, phenylthio, phenoxy, and the phenyl radicals in turn may bear from one to three of the following groups: $C_1$–$C_4$-alkyl, $C_1$–$C_4$-alkoxy, $C_1$–$C_4$-haloalkyl, $C_1$–$C_4$-haloalkoxy, halogen, cyano or nitro;

$R^2$ is hydrogen, hydroxyl, $C_1$–$C_8$-alkoxy, $C_3$–$C_8$-alkenyloxy, di-$C_1$–$C_4$-alkylamino, $C_1$–$C_{25}$-alkyl, $C_3$–$C_{25}$-alkenyl, $C_3$–$C_{25}$-alkynyl or $C_3$–$C_8$-cycloalkyl, where these organic radicals may carry from one to five halogen atoms and/or from one to three of the following radicals: cyano, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, phenyl, phenylthio, phenoxy, and the phenyl radicals in turn may bear from one to three of the following groups: $C_1$–$C_4$-alkyl, $C_1$–$C_4$-alkoxy, $C_1$–$C_4$-haloalkyl, $C_1$–$C_4$-haloalkoxy, halogen, cyano or nitro;

$R^2$ is, further, substituted $C_1$–$C_8$-alkoxy, $C_3$–$C_8$-alkenyloxy, di-$C_1$–$C_4$-alkylamino, $C_1$–$C_{25}$-alkyl, $C_3$–$C_{25}$-alkenyl, $C_3$–$C_{25}$-alkynyl or $C_3$–$C_8$-cycloalkyl, where these groups are substituted by from one to five halogen atoms and/or by one or two 5- to 6-membered heterocyclic radicals selected from the group consisting of 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrazolyl, 4-pyrazolyl, 5-pyrazolyl, 2-pyridyl, 4-pyridyl, oxa-2,4-diazolyl, oxa-3,4-diazolyl, thia-2,4-diazolyl, thia-3,4-diazolyl and triazolyl;

and which radicals may bear one or two of the following substituents: halogen, $C_1$–$C_3$-alkyl or $C_1$–$C_3$-alkoxy;

$R^3$–$R^6$ are each hydrogen, $C_1$–$C_4$-alkyl, $C_1$–$C_4$-alkoxy, $C_1$–$C_4$-haloalkyl, $C_1$–$C_4$-haloalkoxy, $C_1$–$C_4$-alkylthio, $C_1$–$C_4$-haloalkylthio, fluorine, chlorine, bromine, cyano or nitro;

X is oxygen or sulfur;

and an environmentally tolerated salt thereof.

* * * * *